US00PP25018P3

(12) United States Plant Patent
Eubanks

(10) Patent No.: US PP25,018 P3
(45) Date of Patent: Oct. 28, 2014

(54) GAMAGRASS CULTIVAR NAMED 'EAGLE POINT DEVIL CORN'

(50) Latin Name: ***Tripsacum* sp.**
Varietal Denomination: Eagle Point Devil Corn

(71) Applicant: Mary Wilkes Eubanks, Durham, NC (US)

(72) Inventor: Mary Wilkes Eubanks, Durham, NC (US)

( * ) Notice: Subject to any disclaimer, the term of this patent is extended or adjusted under 35 U.S.C. 154(b) by 0 days.

(21) Appl. No.: 13/694,073

(22) Filed: Oct. 31, 2012

(65) Prior Publication Data

US 2014/0123357 P1 May 1, 2014

(51) Int. Cl.
*A01H 5/00* (2006.01)

(52) U.S. Cl.
USPC ..... Plt./384

(58) Field of Classification Search
USPC ..... Plt./384
See application file for complete search history.

*Primary Examiner* — Annette Para

(57) ABSTRACT

A new and distinct gamagrass, which is the product of a cross between gamagrass, *Tripsacum dactyloides*, and a *Zea-Tripsacum* recombinant. This plant is fertile, has proven to be cross compatible with *Zea mays* L. and *Tripsacum* sp., and offers an avenue to expand the gene pool for commercial corn varieties. The instant plant is perennial with well developed rhizomes, aerenchyma tissue in its roots, high carbohydrate and sugar content, abundant seed and prolific vegetation production, traits that give it improved value as a forage crop and biofuel feedstock.

6 Drawing Sheets

Figure 1:
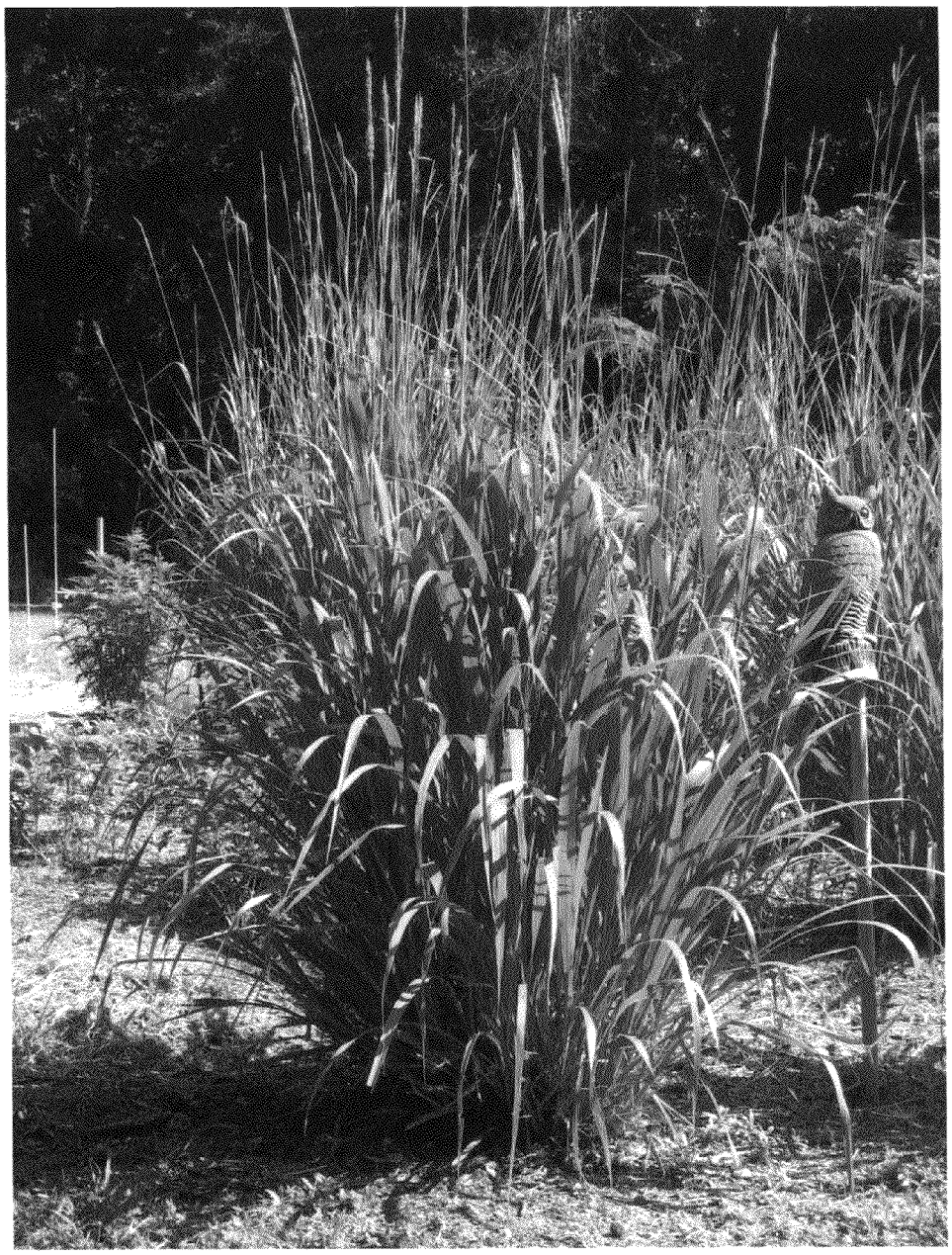

References Cited:

U.S. PATENT DOCUMENTS

| | |
|---|---|
| U.S. Plant Pat. No. 6,906 July 1989 Eubanks | Plt. 89 |
| U.S. Plant Pat. No. 7,977 September 1992 Eubanks | Plt. 89 |
| U.S. Plant Pat. No. 9,640 September 1996 Eubanks | Plt. 100 |
| U.S. Plant Pat. No. 17,444 February 2007 Eubanks | Plt. 258 |

OTHER PUBLICATIONS

Comis, D. 2005. Eastern gamagrass may be queen of carbon storage. Agricultural Research 53: 7.

Douglas J L, 2000. Eastern gamagrass as a potential biofuel crop. USDA-NRCS Tech Rep 15: 27-37, Jamie L. Whitten Plant Materials Center, Coffeeville, Miss.

Eubanks, M. W. 2001. The origin of maize: Evidence for *Tripsacum* ancestry. Plant Breeding Reviews 20:15-66.

Eubanks, M. W. 2006. A genetic bridge to utilize *Tripsacum* germplasm in maize improvement. Maydica 51: 315-327.

Grabowski, J. M., S. D. Edwards and J. L. Douglas. 2004. Evaluation of warm season grass species and management practices to improve biomass production potential in the Mid-South. USDA-NRCS Jamie L. Whitten Plant Materials Center, Coffeeville, Miss., Available online at http://plant-materials.nrcs.usda.gov/mspmc/publications.html#TN, accessed 12 Oct. 2012.

Hill G M, Gates R N, Burton G W, 1993. Forage quality and grazing steer performance from Tifton 85 and Tifton 78 Bermuda grass pastures. Journal of Animal Science 71: 3219-3225.

Hinchman, R. R., M. C. Negri and E. G. Gatliff. 1999. Phytoremediate: Using green plants to clean up contaminated soil, groundwater, and wastewater. Presented at the IBC 4th International Conference on Phytoremediation, Toronto, Calif. Available online at http://citeseerx.ist.psu.edu accessed 12 Oct. 2012.

Mangelsdorf, P. C. 1974. Corn: Its Origin, Evolution and Improvement, Harvard University Press, Cambridge, Mass.

Mashingo, M. S. H., D. W. Kellogg, W. K. Coblentz, K. S. Anschutz. 2008. Effect of harvest dates on yield and nutritive value of eastern gamagrass. Professional Animal Science 24: 363-273.

Owsley C M, 2008. Eastern gamagrass forage performance at Jimmy Carter Plant Materials Center Americus Georgia. USDA-NRCS Misc Tech Art, Available online at http://plantmaterials.nrcs.usda.gov/gapmc/publications.html#TN, accessed 12 Oct. 2012.

Parrish, D. J. and J. H. Fike. 2005. The biology and agronomy of switchgrass for biofuels. Critical Reviews of Plant Science 24: 423-459.

Van der Grinten, M., 2007. Eastern gamagrass: A plant for forage, conservation, and bioenergy. USDA-NRCS, Big Flats Plant Materials Center at Corning, N.Y. Available online at http://plants.usda.gov/8083.pdf; accessed 29 Jun. 2012.

Walsh, Bryan. 2011. Parched earth. *Time*, August 22, pp. 40-45.

Weimer, P. J. and T. L. Springer, 2007. Fermentability of eastern gamagrass, big bluestem and sand bluestem grown across a wide variety of environments. Bioresource Technology 98: 1615-1621.

BACKGROUND OF THE NEW PLANT

Gamagrass, *Tripsacum* sp., is a polyploid, rhizomatous, perennial C4 grass closely related to corn (*Zea mays* L.) It has a base chromosome number x=18 and varying ploidy levels that range from 2n=36 to 2n=108. *Tripsacum* species are highly variable in form, vigor, and ecological adaptation. The endemic ranges for *Tripsacum* are from Canada to Chile. It is adapted to wide variation in elevations and habitats including swampy sites, deciduous forests, prairie, sandy soils, tropical forests, and near-desert conditions (Eubanks 2001).

This application describes a new gamagrass cultivar produced by crossing Eastern gamagrass, *T. dactyloides* L., with a recombinant plant that has genes from perennial teosinte (*Zea diploperennis* Iltis, Doebley and Guzman), maize (*Zea mays* L.), and gamagrass, (*T. dactyloides*).

Eastern gamagrass is a warm season perennial bunchgrass valued for its use as silage and hay for beef and dairy cows (van der Grinten et al. 2007). It has potential to produce large amounts of biomass in the southeastern United States. Some of its many desirable characteristics as an energy crop include high biomass yield potential, persistence, adaptation to different soil and climate conditions, non-invasiveness, carbon sequestration capacity, soil phytoremediation ability, and easy integration into existing farming operations (Douglas 2000; Grabowski et al. 2004; Hinchman et al., 1999; Mashingo et al. 2008; van der Grinten 2007; Weimer and Springer 2007). Gamagrass yields of up to 24,965 kg/ha (Owsley 2008) are comparable to those of switchgrass and bermudagrass (Parrish and Fike 2005; Hill et al. 1993).

Diploid perennial teosinte, *Zea diploperennis* Iltis, Doebley and Guzman (hereafter referred to as diploperennis), is a wild relative of corn that was unknown until it was discovered on the threshold of extinction in the mountains of Jalisco, Mexico in the late 1970's (ltis et al. 1979). It is in the same genus as corn, has the same chromosome number (2n=20), and hybridizes easily with corn. Crosses between corn and Eastern gamagrass generally produce hybrids that are male sterile and essentially female sterile. Early attempts to cross *Tripsacum* and the wild *Zeas* referred to as teosinte, failed (Mangelsdorf 1974). In 1985, Eubanks recovered viable, fertile hybrids from crosses between diploperennis and Eastern gamagrass and (Eubanks 1989, 1992, 1996, 2007). These gamagrass-teosinte recombinants are cross fertile with corn, teosinte, and gamagrass.

The new plant is a gamagrass cultivar introgressed with *Zea* genes by crossing a *Tripsacum dactyloides* L. plant (referred to as 'Eagle Point'), with '7022*Devil Corn', a plant produced by pollinating the silks of a corn-Tripsacorn hybrid (referred to as '7022'), with pollen from a gamagrass-diploperennis recombinant (referred to as 'Devil Corn').

On Jul. 24, 2003, Eubanks pollinated 'Eagle Point' *Tripsacum dactyloides* with pollen from '7022*Devil Corn'. The seed germinated in a petri dish Nov. 24, 2003, was placed in pot in potting soil Dec. 4, 2003, and grown in a greenhouse in Durham, N.C. The seedling developed into a normal, fully fertile plant that is perennial and produces viable fruits year-round in the greenhouse. The plants have been propagated by rhizome divisions and planted in Durham, N.C., Lumberton, Miss., and Austin, Tex., where they have been continuously maintained in outdoor nurseries. This new *Tripsacum-Zea* recombinant expands the genetic diversity for crosses between *Tripsacum* and *Zea* via conventional hand pollination technique. It enhances the link between the wild relatives and modern corn, which promises to be beneficial in corn improvement breeding programs. Unique propagation of this plant through successive generations by means of rhizome divisions has demonstrated that the new plant not only retains continuous and abundant production capability, but also has distinguishing characteristics that hold true from generation to generation and appear to be firmly fixed.

Examination of the roots revealed that 'Eagle Point Devil Corn' (referred to hereafter as EPDC) has well developed air passages, referred to as aerenchyma, in its roots. This property provides oxygen to roots enabling them to survive anaerobic conditions as in flooded soils (Comis 2005). It also allows the roots to grow deep below the hardpan. This deep-rooting characteristic conveys outstanding drought tolerance. The plant tolerates acid soil and aluminum, making it a good candidate for phytoremediation of contaminated soils and wastewater (Eubanks 2006; Hinchman et al. 1999).

EPDC plants exhibited exceptional drought and heat tolerance in 2011 in the *Tripsacum* nursery at the Brackenridge Field Laboratory, Austin, Tex. In 2011, Central Texas experienced exceptional (D4) drought, the most severe ranking by the National Drought Mitigation Center (Walsh 2011). It was the worst one-year drought on record. With just 6.5 in (17 cm) of rain since November 2010, the 2011 growing season began with a 27.5 in (68.7 cm) water deficit. Texas also experienced record-shattering heat in 2011 with 90 days of temperatures from 100° F. (37° C.) to 112° F. (44.4° C.). EPDC plants survived the drought and heat without supplemental water from June to August.

Chemical analysis revealed EPDC has higher carbohydrate and sugar content than its gamagrass parent. The EPDC total carbohydrates (lignin, ash, glucan and xylan) are 94.1 percent of biomass dry weight. This exceeds its gamagrass parent by 13%. Due to its high carbohydrate content and higher carbohydrate conversion (83.8%), EPDC produces higher sugar yields. Glucose is 410.1 mg $m^{-1}$ raw biomass, xylose is 169.5 mg $m^{-1}$ raw biomass, and total sugars are 595.8 mg $m^{-1}$ raw biomass. The EPDC sugar yield is 51.6% greater than switchgrass, a prevalent biofuel feedstock.

EPDC Propagation has taken place in Durham, N.C., Lumberton, Miss., and Austin, Tex.

DESCRIPTION OF ILLUSTRATIONS

Figure 2:
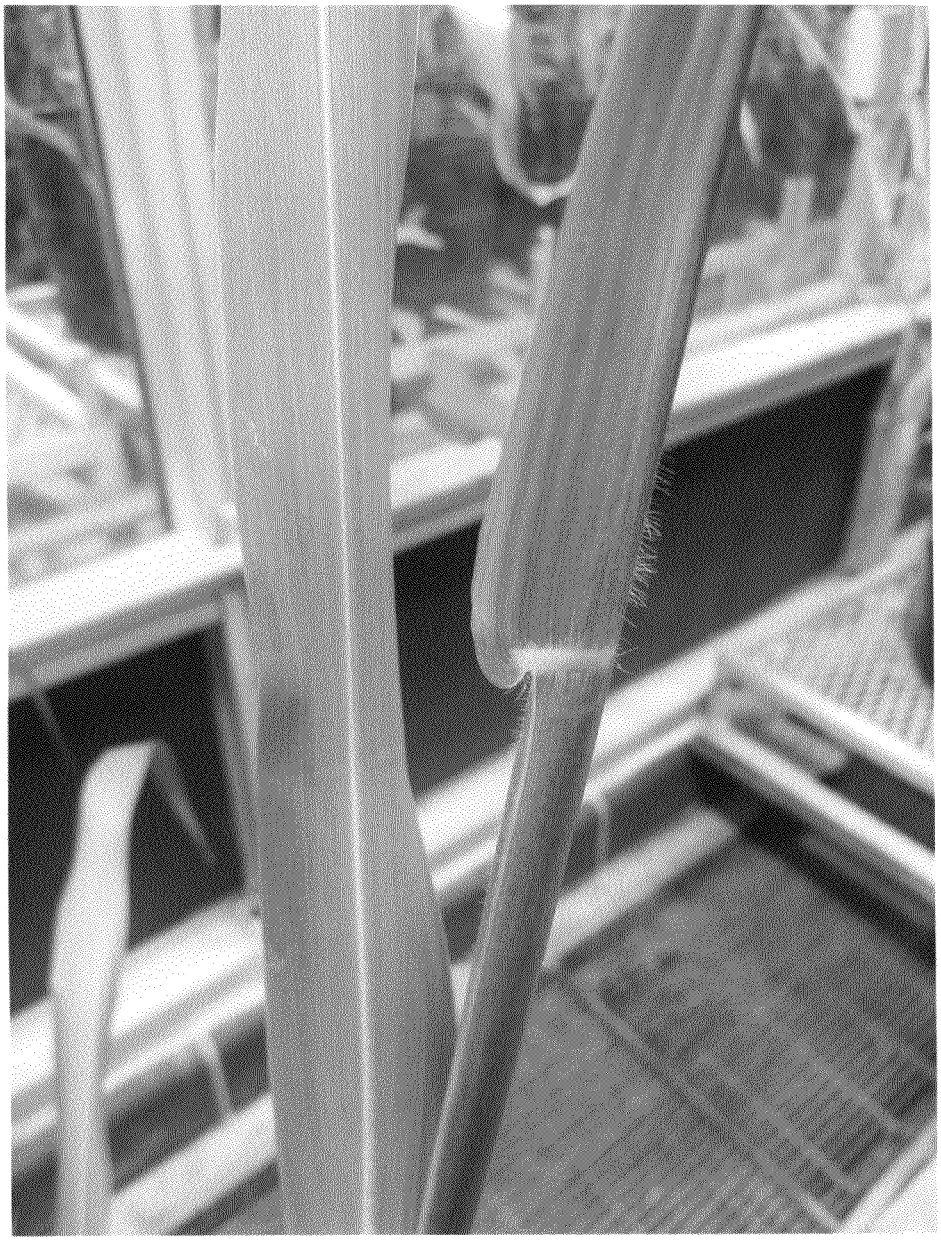
Figure 3:
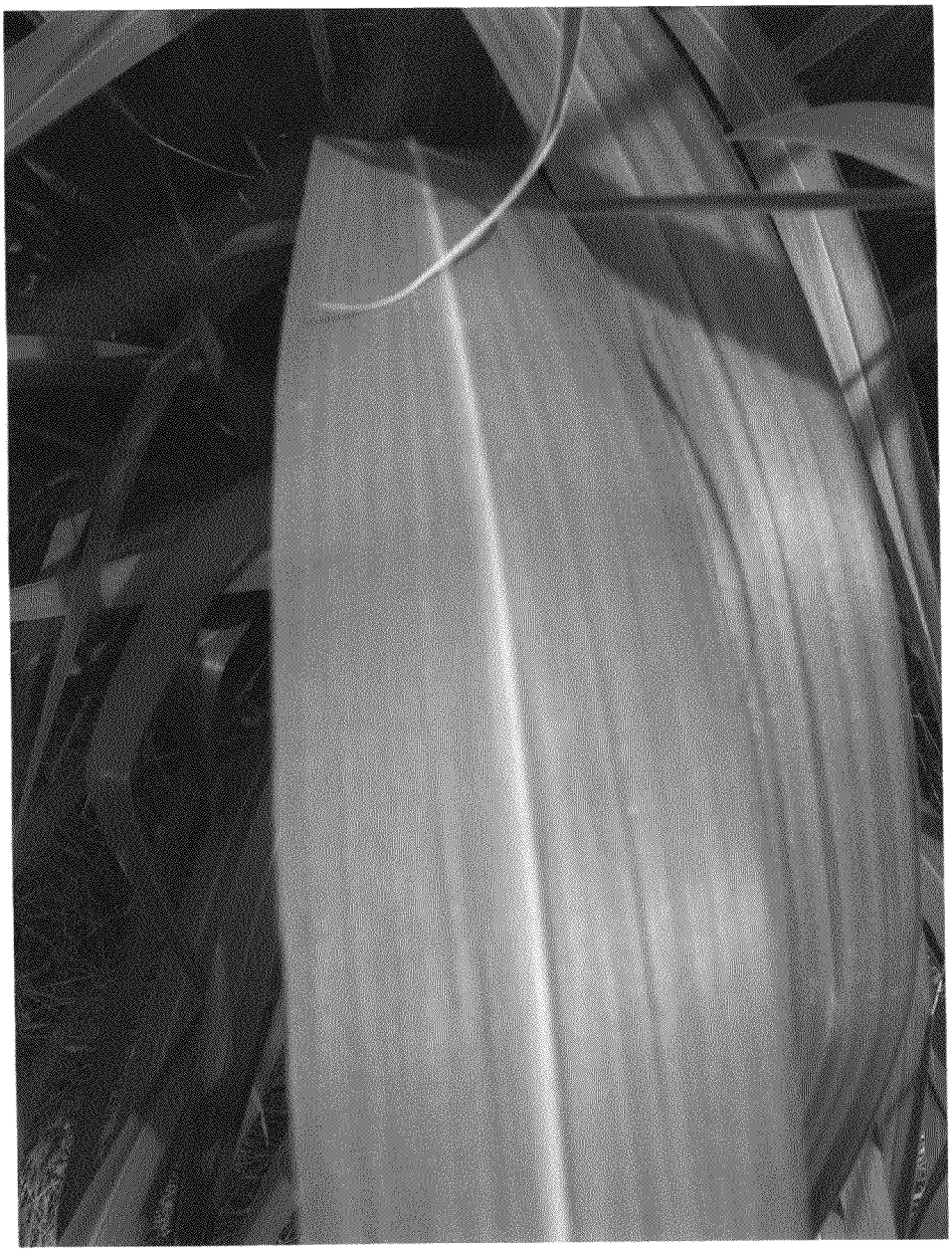
Figure 4:
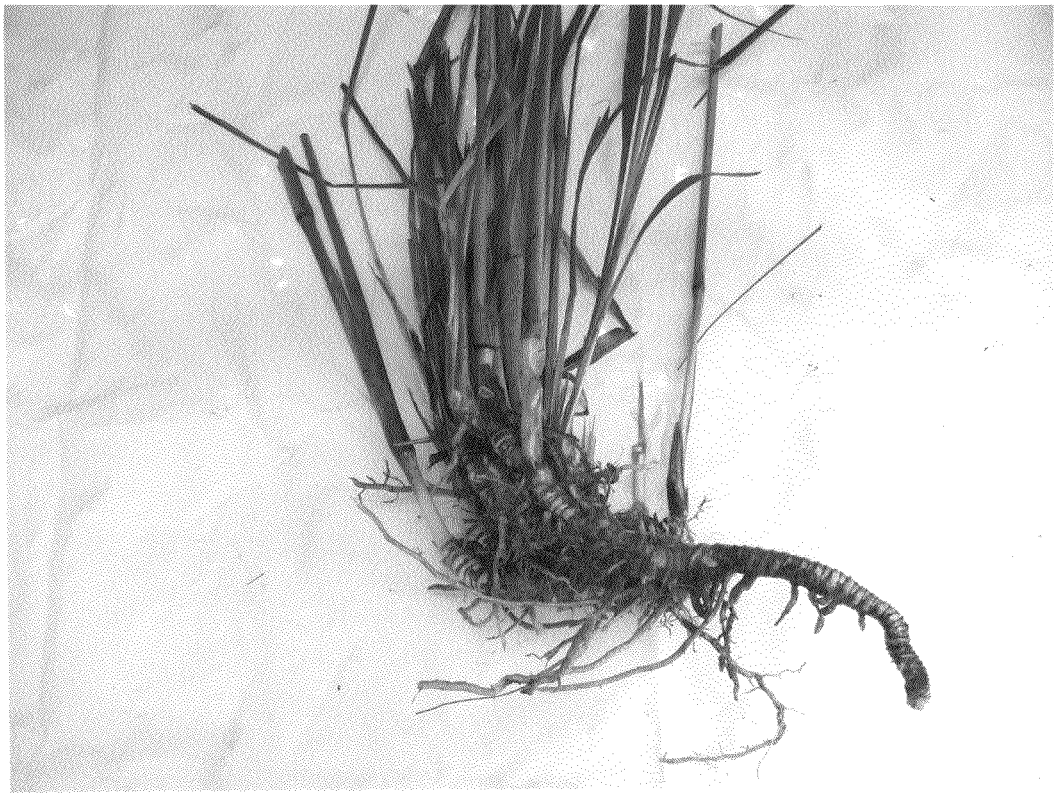
Figure 5:
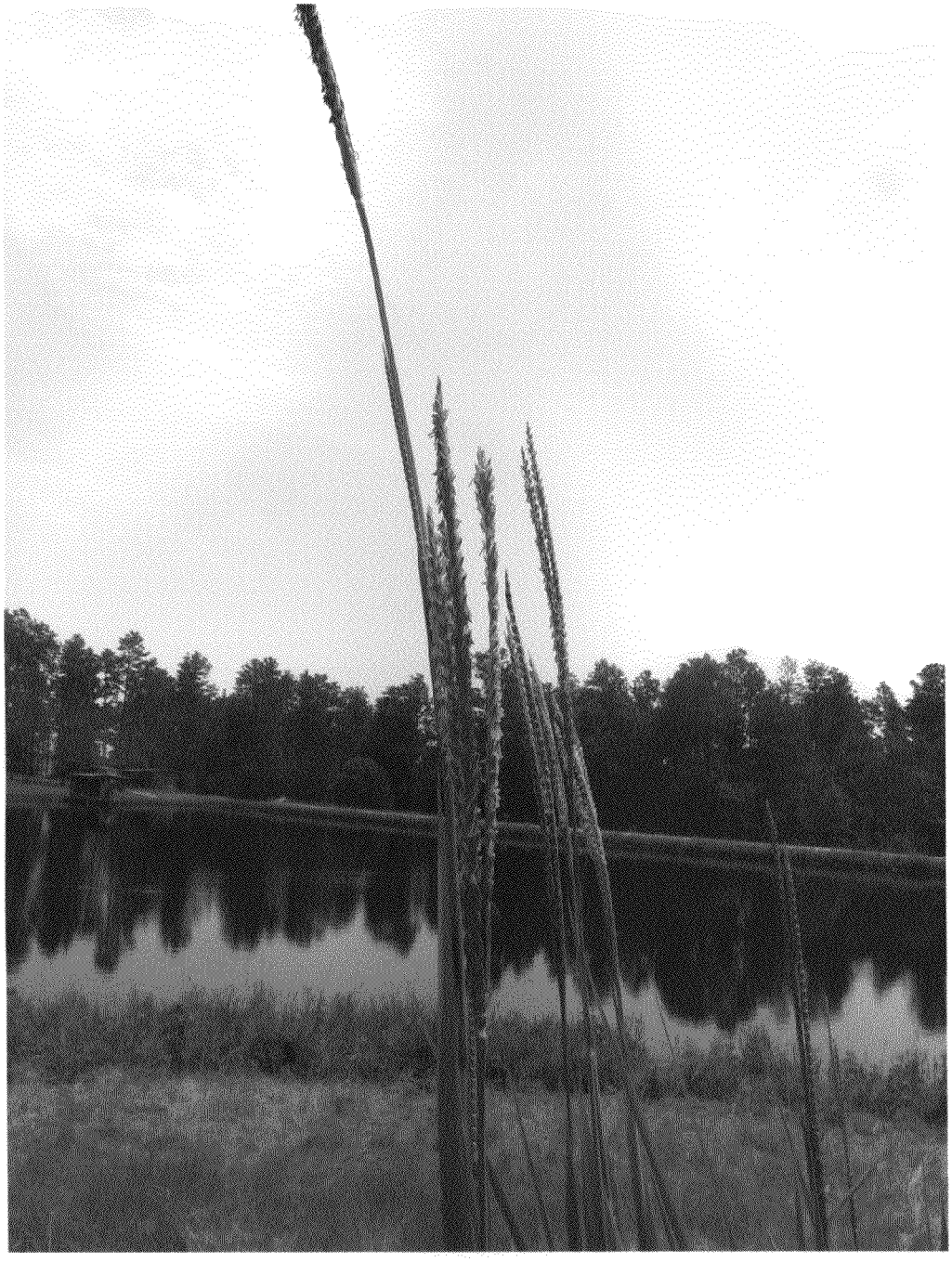

This new gamagrass plant is illustrated by the accompanying full color photographs that include:

FIG. 1 a fully grown plant showing the characteristic habit of many culms growing from the base;

FIG. 2 close-up of culms enwrapped by pubescent sheath;

FIG. 3 close-up of the midrib and leaf margins;

FIG. 4 rhizome;

FIG. 5 flowering spike, and

Figure 6:
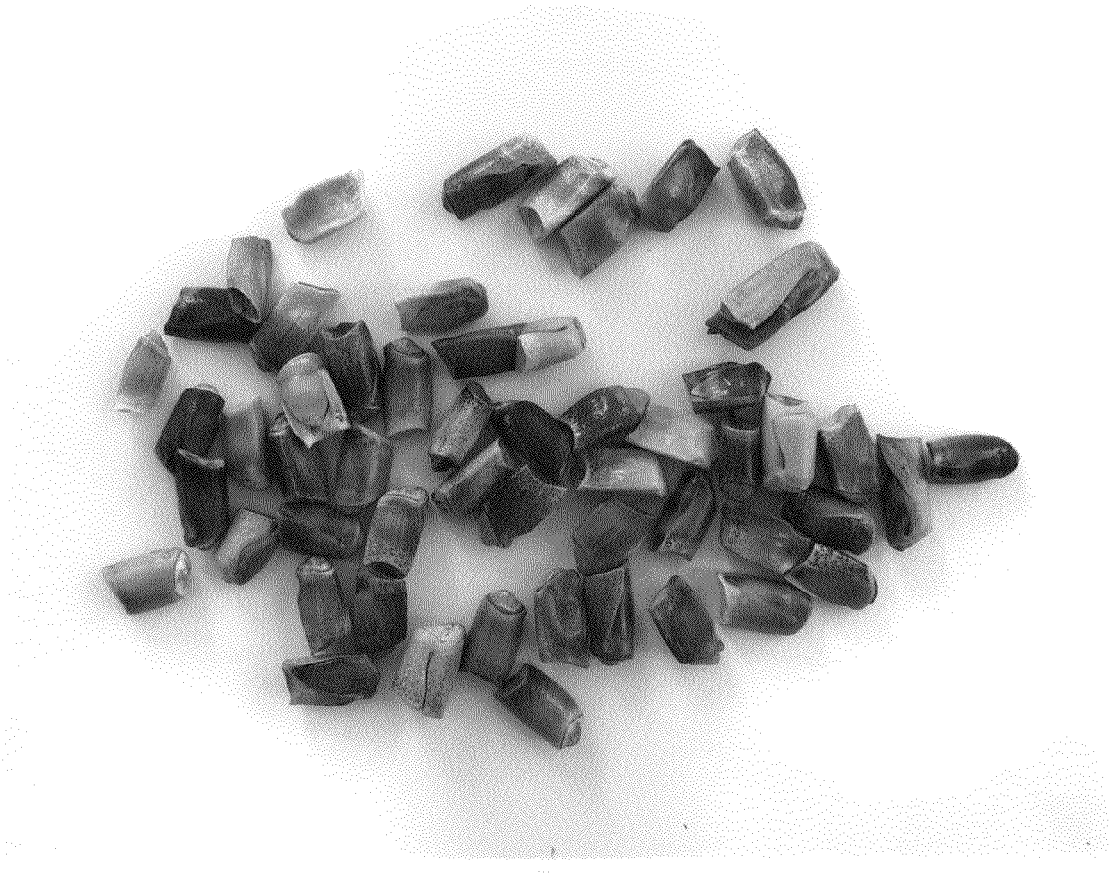

FIG. 6 mature seeds.

THE PLANT

Origin: Seedling.

Parentage:

*Seed parent.*—*Tripsacum dactyloides* (x=18) 'Eagle Point'. Provenance: Ocean Springs, Davis Bayou, Jackson County, Miss.

*Pollen parent.*—'7022*Devil Corn' (2n=20). Provenance: cross between the female parent '7022', which is a cross between Tripsacorn (Eubanks 1992, U.S. Plant Pat. No. 7,977) and pollen donor maize inbred line W64a, with pollen donor 'Devil Corn', which is a cross between female parent *T. dactyloides* and pollen donor 'Tripsacorn', that was then backcrossed once with pollen from 'Tripsacorn'.

Classification:

*Botanic.*—*Tripsacum dactyloides.*

Habit: Essentially erect; as many as 117 primary culms.

Duration:

*Perennial.*—Sends out shoot from rhizomes, essentially upright, dies back in winter and produces new growth in the spring, grows year-round in a greenhouse.

*Plant dimensions.*—2.5 m high×2.3 m wide.

*Wet weight biomass at peak growth.*—15.8 kg (34.9 lb).

*Dry weight biomass at peak growth.*—5.1 kg (11.1 lb).

*Moisture.*—68%.

Culm:

*Height.*—Up to 2.5 meters long: slender, simple with branching from the nodes of the flowering spike; glabrous; round to slightly oval in cross section; Diameter 0.98 cm×0.82 cm.

*Color.*—Green (Pantone #16-0532 TP "Moss").

*Internode.*—Glabrous; length 24.5 cm.

*Sheath.*—Ciliate, tightly enwraps the culm, margins not united; Color: deep red (Pantone #19-1617 TP "Burgundy") to medium red (Pantone #18-1418 TP "Crushed Berry").

*Ligule.*—Present on adaxial side of leaf at junction of blade and sheath; length: 1.8 mm; membranaceous, irregular edge, Color: yellow-green (Pantone #12-0521 TP "Young Wheat").

Leaf blade: Alternate; distichous; sheathing base; narrowly linear, flat, thin.

*Average length.*—90.0 cm. Width: 3.1 cm.

*Color.*—Green (Pantone #18-0328 TP "Cedar Green").

*Leaf margin.*—Scabrous. Color: red (Pantone #19-2431 TP "Boysenberry").

*Midrib.*—Color: white (Pantone #11-0105 TP "Antique White").

*Adaxial surface.*—Glabrous.

*Abaxial surface.*—Glabrous.

*Prominent parallel veins.*—6 per 1.0 cm width.

INFLORESCENCE

Blooming period: Continuous year-round in the greenhouse; in the field early June through October. Flowering begins about two weeks later than the *T. dactyloides* Eagle Point parent.

Monoecious: Separate male and female flowers borne on same plant.

Flowering spike: Borne on a spike at the summit of a culm and on 5 axial flowering branches; spikes at the culm terminus may be single, bifurcated, or trifurcated; axial spikes are single.

*Number of flowering spikes.*—117. Male and female flowers borne on same spike, staminate flowers subtended by the pistillate flowers.

*Total flowering spike length.*—29.0 cm; staminate spike length: 22.5 cm; 55 anther pairs; pistillate spike length: 6.5 cm; 6-7 caryopses.

*Axis.*—Stiff, continuous, ascending.

Staminate flowers:

*Spikelet.*—Two-flowered, both sessile; laterally compressed awnless. Anther length: 7.7 mm. Width: 2.9 mm. In pairs on one side of a persistent central axis.

*Glumes.*—Outer glume: cartilaginous, tapering to a rounded tip, flat. Inner glume: membranaeous. Length: 7.3 mm. Width: 3.2 mm.

*Anther color.*—Yellow (Pantone #13-0633 TP "Chardonnay" when first extrudes, turns to deep wine (Pantone #19-2025 TP "Red Plum") as matures and sheds pollen.

Pistillate flowers: Spikelets distichously arranged; pistillate flower consists of a single rowed spike of 6-7 rectangular caryopses in hard fruit cases; caryopses disarticulate upon maturity.

*Styles.*—Pilose. Length: 2.57 cm.

*Pistil color.*—Ranges from purplish pink (Pantone #17-1718 "Dusty Rose") when fist emerge to wine red (Pantone #19-1530 TP "Burnt Russet") when mature.

Fruit: As many as 16 spikes per culm, each spike bearing 6-7 seeds, approximately 100 seeds per culm or up to 11,700 seeds per plant per blooming period; flowers produced year-round.

*Maturity.*—45 days following fertilization.

*Kernel* (*dried*).—Caryopses in hard, fruit cases, disarticulate upon maturity.

*Size.*—Length: 7.8 mm, Width: 4.7 mm, Thickness: 3.1 mm.

*Shape.*—Rectangular. Color: Ranges from dark brown (Pantone # 181124 TP "Partridge") to medium brown (Pantone # 17-1322TP "Burro") to light brown (Pantone #15-1314TP "Cuban Sand").

*Weight* 20 *seeds* (*unsized sample*).—2.9 gm.

Components (% dry weight raw biomass):

*Acid insoluble lignin.*—23.3.

*Acid soluble lignin.*—3.

*Ash.*—5.8.

*Glucan.*—43.3.

COMPARATIVE PARENTAL CHARACTERISTICS

Duration:

*'Eagle Point' Tripsacum dactyloides.*—Perennial from rhizomes.

'7022*Devil Corn'.—Perennial sends out shoots from underground bulbils adapted to the tropics, does not survive prolonged freezing at or below −2° C.

Plant height:

*'Eagle Point' Tripsacum dactyloides.*—2.6 m.

'7022*Devil Corn'.—1.7 m.

Culm:

*'Eagle Point' T. dactyloides.*—Culm slightly oval in cross section; Diameter: 0.72 cm sheath enwraps the culm. Color: green (Pantone #18-0525 TP "Iguana"), Internode length: 36.2 cm. No ligule at junction of leaf blade and sheath.

'7022*Devil Corn'.—Culm oval in cross section; Diameter: 1.3 cm×1.1 cm; sheath enwraps the culm. Color: dark reddish brown (Pantone #18-1614 TP "Nocturne"), Internode length: 11.2 cm. Ligule present on adaxial side of leaf at junction of leaf blade and sheath; length: 4.3 mm; membranaceous, irregular edge, Color: light green (Pantone #14-0647 TP "Celery").

Leaf blade:

*'Eagle Point T. dactyloides'.*—Length: 142.5 cm. Width 3.7 cm; margins scabrous from midsection of blade to tip; adaxial surface glabrous; veins: 5 per 1.0 cm width; Color: green (Pantone #18-0228 TP "Lime Peel").

'7022*Devil Corn'.—Length: 47.5 cm. Width: 5.0 cm; margins scabrous; adaxial surface glabrous; veins: 4 per 1.0 cm width; Color: green (Pantone #18-0332 TP "Grasshopper").

Blooming period:

*'Eagle Point' T. dactyloides*.—End of May to end of October.

'7022**Sun Devil'*.—From June to August.

Monoecious: 'Eagle Point' *T. dactyloides* and '7022*Sun Devil' have separate male and female flowers borne on same plant.

Flowering spike:

*'Eagle Point' T. dactyloides*.—Borne on a spike at the summit of a culm and on axial flowering branches; spikes at the culm terminus may be single, bifurcated, or trifurcated; axial spikes are single. Number of flowering spikes: 89.

'7022**Sun Devil'*.—Male flowers borne on tassel at culm summit, spikes of female flowers born axillary at nodes along culm; occasional axial pistillate inflorescences have staminate flowers above. Number of flowering spikes: 50.

Staminate flowers:

*'Eagle Point' T. dactyloides*.—Borne above pistillate flowers on a spike with one to three branches. Total length staminate spike: 18.0 cm. Staminate spikelets sessile in pairs. Staminate spikelet outer glume length: 6.1 mm. Width: 3.0 mm. Color: green (Pantone #16-0532 "Moss"). Anther length: 4.4 mm. Color: dark red (Pantone #19-1526 TP "Dark Red Brown").

'7022**Devil Corn'*.—Borne in a terminal inflorescence with 3 to 4 branches at summit of culm.

Pistillate flowers:

*'Eagle Point' T. dactyloides*.—Length pistillate spike: 6.0 cm; pistillate flowers in distichously arranged cupules. Style length: 1.2 mm, Color: purplish red (Pantone #19-1629 TP "Ruby Wine").

'7022**Devil Corn'*.—Pistillate spike borne in leaf axils, pistillate flowers in distichously arranged cupules.

Fruit:

*'Eagle Point' T. dactyloides*.—As many as 10 spikes per culm, each spike bearing 6 seeds, approximately 5,340 seeds per blooming period. Maturity: 45 days following fertilization. Kernel (Dried): Caryopses in hard, fruit cases, disarticulate upon maturity. Size: Length: 11.3 mm. Width: 4.7 mm. Shape: Rectangular. Color: Dark brown (Pantone #19-1116 TP "Olive Brown"), medium brown (Pantone #17-1322 TP "Burro"). Weight 20 seeds (unsized sample): 2.7 g.

'7022**Devil Corn'*.—Caryopses in hard, trapezoidal fruit cases enclosed in a leaf sheath, disarticulate upon maturity. Maturity: 45 days following fertilization. Kernel (Dried): Size: Length: 7.5 mm. Width: 4.9 mm. Color: black (Pantone #19-1314 TP "Seal Brown" to dark brown (Pantone #19-1241 TP "Tortoise Shell"). Weight 20 seeds (unsized sample): 1.8 g.

Color reference: The Pantone Textile Color Guide. 1992. Pantone, Inc., Carlstadt, N.J. ISBN 1-881509-32-X.

COMPARISON OF EAGLE POINT DEVIL CORN TO PARENT PLANTS

Although the 'Eagle Point Devil Corn' plant most closely resembles its 'Eagle Point' *T. dactyloides* parent phenotypically, it is distinctive from 'Eagle Point' *T. dactyloides* in its later flowering date, more upright habit, greater number of culms, more profuse seed production, higher lignin, ash and glucan content. 'Eagle Point' *T. dactyloides* flowers from May to October and 'Eagle Point Devil Corn' flowers June to October. '7022*Devil Corn' flowers June to August. 'Eagle Point Devil Corn' produces around 117 flowering spikes compared to 'Eagle Point' *T. dactyloides* which produces 89 flowering spikes and '7022*Devil Corn' which produces 50. 'Eagle Point Devil Corn' is intermediate between the two parents in internode length and leaf length. The 'Eagle Point Devil Corn' internode length is 24.5 cm compared to 'Eagle Point' *T. dactyloides* at 36.2 cm and '7022*Devil Corn' at 11.2 cm. 'Eagle Point Devil Corn' leaf length averages 90.0 cm compared to 'Eagle Point' *T. dactyloides* at 142.5 cm and '7022*Devil Corn' at 47.5 cm. 'Eagle Point' *T. dactyloides* is liguless. 'Eagle Point Devil Corn' has a ligule like its '7022*Devil Corn' parent but its ligule length is 1.8 cm compared to a ligule length of 4.3 cm in 7022*Devil Corn. 'Eagle Point Devil Corn' produces 11,700 seeds per plant compared to 5,340 seeds per plant for its 'Eagle Point' *T. dactyloides* parent. The greater number of culms and plant biomass give 'Eagle Point Devil Corn' added value as a forage crop and a highly productive biofuel crop. Due to its high sugar content (glucose 410.1 mg $m^{-1}$ raw biomass, xylose 169.5 mg $m^{-1}$ raw biomass, and total sugars 595.8 mg $m^{-1}$ raw biomass) with a theoretical yield of 102 gallons ethanol per ton of biomass, 'Eagle Point Devil Corn' is a promising high-yield biofuel feedstock.

I claim:

1. A new and distinct variety of gamagrass, substantially as herein shown and described that is characterized by its profuse production of fruit and plant biomass, its high carbohydrate and sugar content, its upright, perennial habit, roots with well-developed aerenchyma, its combining ability with corn that permits movement of new genetic diversity into corn using conventional plant breeding methods.

* * * * *